(12) United States Patent
Desinger et al.

(10) Patent No.: US 8,157,799 B2
(45) Date of Patent: Apr. 17, 2012

(54) BIPOLAR COAGULATION ELECTRODE

(75) Inventors: Kai Desinger, Berlin (DE); Thomas Stein, Berlin (DE); Andre Roggan, Berlin (DE)

(73) Assignee: Celon AG Medical Instruments (DE)

( * ) Notice: Subject to any disclaimer, the term of this patent is extended or adjusted under 35 U.S.C. 154(b) by 0 days.

(21) Appl. No.: 13/071,645

(22) Filed: Mar. 25, 2011

(65) Prior Publication Data

US 2011/0172661 A1    Jul. 14, 2011

Related U.S. Application Data

(60) Division of application No. 11/631,836, filed as application No. PCT/EP2005/053255 on Jul. 7, 2005, now abandoned, and a continuation-in-part of application No. 10/806,867, filed on Mar. 23, 2004, now abandoned, which is a division of application No. 09/868,303, filed on Jul. 30, 2001, now Pat. No. 6,723,094.

(30) Foreign Application Priority Data

Dec. 18, 1998    (DE) .............................. 198 58 599 U
Jul. 7, 2004      (DE) ......................... 10 2004 033 595

(51) Int. Cl.
*A61B 18/14*    (2006.01)

(52) U.S. Cl. ........................................................ 606/50
(58) Field of Classification Search .................... 606/48, 606/50
See application file for complete search history.

(56) References Cited

U.S. PATENT DOCUMENTS

| | | | | |
|---|---|---|---|---|
| 3,920,021 | A * | 11/1975 | Hiltebrandt | 606/50 |
| 4,682,596 | A * | 7/1987 | Bales et al. | 606/39 |
| 5,277,696 | A * | 1/1994 | Hagen | 606/49 |
| 5,348,554 | A * | 9/1994 | Imran et al. | 606/41 |
| 5,647,871 | A * | 7/1997 | Levine et al. | 606/45 |
| 5,688,267 | A * | 11/1997 | Panescu et al. | 606/41 |
| 5,951,546 | A * | 9/1999 | Lorentzen | 606/41 |
| 6,514,251 | B1 * | 2/2003 | Ni et al. | 606/41 |
| 6,723,094 | B1 * | 4/2004 | Desinger | 606/50 |
| 7,052,494 | B2 * | 5/2006 | Goble et al. | 606/45 |
| 7,192,429 | B2 * | 3/2007 | Trembly | 606/41 |

* cited by examiner

*Primary Examiner* — Lee Cohen
(74) *Attorney, Agent, or Firm* — Ostrolenk Faber LLP

(57) ABSTRACT

The invention concerns a bipolar coagulation probe (10) having an electrode tip (14) which has an end face (16) in which a pole (17) of a first electrode (18) and a pole (19) of a second electrode (20) are integrated. In accordance with the invention the bipolar coagulation probe (10) includes a temperature control unit (26) with a temperature control medium for temperature control of the end face (16).

11 Claims, 2 Drawing Sheets

BIPOLAR COAGULATION ELECTRODE

CROSS-REFERENCE TO RELATED APPLICATION

Figure 1:
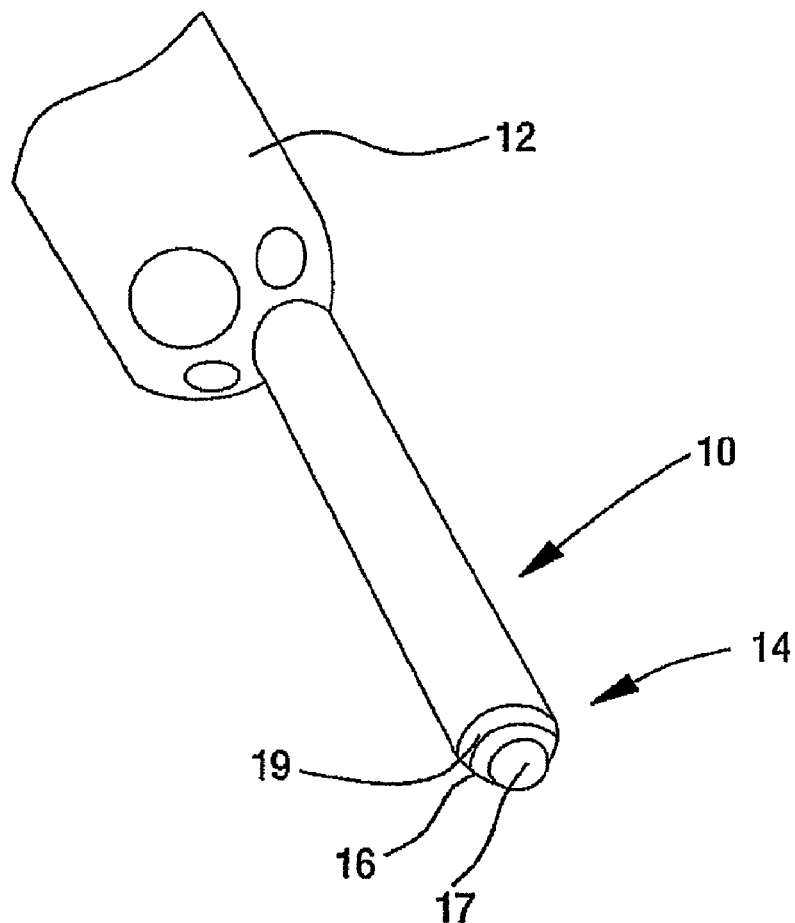

This application is a divisional application of U.S. Ser. No. 11/631,836, (abandoned), which was filed Oct. 9, 2007, which in turn is a National stage of International application no. PCT/EP2005/053255 filed Jul. 7, 2005 which claims priority to German patent application no. 102004033595.8. U.S. application Ser. No. 11/631,836, (abandoned) is also a Continuation-in-Part (CIP) application of U.S. Ser. No. 10/806,867, (abandoned) filed Mar. 23, 2004, which in turn, is a divisional application of U.S. Ser. No. 09/868,303, which was filed Jul. 30, 2001, and which ultimately issued as U.S. Pat. No. 6,723,094, on Apr. 20, 2004. The Ser. No. 09/868,303 application claims priority to PCT/EP99/10079 filed Dec. 17, 1999, which in turn, claims priority to DE 198 58 599.3, filed Dec. 18, 1998.

The invention concerns a bipolar coagulation electrode which is suitable for use in minimally invasive surgery.

The care of peri-operative hemorrhages is part of any surgical intervention. In recent years bipolar high frequency coagulation has developed into a standard method for blood coagulation. The coagulation electrodes used include at least two electrode poles, between which a high frequency ac voltage can be applied and which are disposed in a common instrument. The two electrode poles are connected for example to mutually insulated arms of a bipolar pair of tweezers or can be embodied in a coaxial arrangement in a so-called coagulation pencil. An advantage of the bipolar procedure is that a flow of current takes place only between the closely adjacent poles of the electrodes and not through the entire body of the patient. Burning effects due to improperly fixed neutral electrodes or unintended grounding of the patient, as are possible with monopolar high frequency surgery, are also prevented.

The previous bipolar coagulation electrodes of conventional configuration are not suitable for some areas of minimally invasive surgery, in particular endoscopic neurosurgery. Therefore, bipolar coagulation probes with a spherical end face have been developed, with a pole of a first electrode and a pole of a second electrode being integrated in the end face. Use of the coagulation probe in minimally invasive surgery is substantially facilitated with the spherical configuration of the end face. The spherical surface configuration of the end face permits particularly simple handling of the coagulation probe. The spherical end face further permits surface coagulation even when the shank is not held perpendicularly to the surface of the tissue.

The known bipolar coagulation probes with an active end face however suffer from the disadvantage that, in regular proper use, the tissue can adhere to the poles of the electrodes.

The object of the present invention is to overcome the disadvantages of the state of the art.

In accordance with the invention that object is attained by a bipolar coagulation probe as set forth in claim 1. The bipolar coagulation probe according to the invention has a shank with a distal end which has an end face in which a pole of a first electrode and a pole of a second electrode are integrated. The bipolar coagulation electrode is distinguished in that it includes a temperature control unit. In that way the detrimental adhesion of tissue to the poles of the electrodes, which is known from conventional electrosurgery, can be reduced or indeed entirely eliminated. In the case of a coagulation probe which does not afford temperature control, the highest temperature during the coagulation procedure prevails in the region of the tissue which bears against the poles of the electrodes. With increasing drying-out of the tissue it begins to adhere to the poles of the electrodes. The temperature control unit according to the invention however means that the temperature at the poles can be reduced to such an extent that it is no longer possible for the tissue to stick to the poles of the electrodes. Temperature control of the poles of the electrodes at a temperature which is below the temperature that is critical for tissue adhesion provides that the zone of the critical temperatures is displaced away from the poles into deeper tissue layers. In that case the temperature control unit serves for cooling at least the distal end of the coagulation probe. In addition, the temperature control unit according to the invention makes it possible for the temperatures of the end face of the electrode tip to be adjusted and maintained during and prior to coagulation as well as upon introduction of the electrode into the body. In particular it is also possible for the coagulation probe to be heated prior to an application. A coagulation probe without a temperature control unit according to the invention only warms up upon tissue contact as it is only then that a high frequency current can flow, which provides for an increase in tissue temperature and thus indirectly leads to an increase in the temperature of the coagulation probe. For some applications however it is desirable if the coagulation probe is already at a desired temperature immediately at the beginning of an application and not just after a time delay caused by indirect heating thereof.

The temperature control unit according to the invention is designed in such a way that it can guide a temperature control medium to the distal end of the bipolar coagulation probe in order to cool or heat the end face. The temperature control medium is a fluid which is suitable for receiving and delivering thermal energy. The temperature control unit can include usual means for setting a temperature which is to be predetermined or a predeterminable temperature profile for the temperature control medium such as for example an optionally controllable thermostat, or it can be connected to such means. Temperature control of the end face, in only regionwise manner, may be sufficient for the purposes according to the invention so that the temperature control medium does not inevitably have to be in heat exchange relationship with the entire end face of the bipolar coagulation electrode. It is in particular temperature control of the poles of the bipolar coagulation electrode, which are disposed in the end face, that is to the fore.

Preferably the temperature control unit includes a guide structure for the temperature control medium, with which the temperature control medium is guided to the rear side of the end face in the interior of the distal end of the coagulation probe and there at least partially deflected and guided back again. The temperature control medium thus flows along the rear side of the end face and in that way quickly and effectively removes the heat which is produced in the coagulation operation, or heats the end face to the desired temperature.

In accordance with a preferred first variant the temperature control medium for the temperature control unit is a sterile, pyrogen-free physiological saline solution. That ensures that, in the event of a defect with the coagulation electrode and in the event of the related escape of the temperature control medium into the patient, there is no risk to health. The temperature control medium is also electrically conductive. If therefore, in accordance with a further preferred embodiment of the invention, there are bores at the end face of the electrode tip, in particular in the poles, through which the temperature control medium at least partially issues, the tissue drying-out effect which occurs upon considerable heating of the tissue can be compensated and the application of electrical energy can be improved by maintaining the electrical conductivity of the tissue.

In accordance with a preferred second variant deionised water is used as the temperature control medium. That has the advantage that it is possible to dispense with electrical insulation for the poles in relation to the temperature control medium for the conductivity of deionised water is sufficiently low for the purposes of the invention. Cooling and heating of the end face, in particular directly in the region of the poles, can be implemented in that way highly effectively and without complicated and expensive structural adaptation of the electrode construction.

Preferably the temperature control unit is connected to a peristaltic pump for conveying the temperature control medium. Peristaltic pumps have the advantage that the mechanism of the pump does not come into contact with the fluid to be pumped. Sterile fluids thus remain sterile, assuming that a sterile tube is used. Maintaining the sterility of the temperature control medium enhances the safety of the system. Thus there is no risk of infection if the temperature control medium escapes into the body of the patient due to a defect.

The end face is the face which is visible from a point of view on the longitudinal axis of the shank, which is prolonged in the distal direction, when the view is in the proximal direction of the shank.

In accordance with a further preferred embodiment of the invention the end face of the coagulation probe according to the invention is spherically shaped. The term 'spherical end face' is used to denote an at least approximately ball-shaped region of the electrode tip. In that respect the spherical end face can form for example the distal end of the shank in the form of a hemisphere. The configuration however is not restricted to contours which are spherical in the geometrical sense, but it can also be of a surface curvature which deviates therefrom. The spherical end face is rounded off in the direction of the adjoining shank of the electrode tip and does not have any portions extending perpendicularly to the longitudinal axis. The surface of the spherical end face does not have to be completely smooth but can also be contoured to a slight degree, for example by slightly raising the poles of the electrodes out of the plane of the end face.

The term 'pole' is used to denote the part of the electrode, which in the application forms an electrically active surface in relation to the surrounding tissue, that is to say that surface region in which electrical energy is caused to pass into the surrounding tissue when an ac voltage is applied.

In accordance with a preferred configuration of the invention the electrical pole of the second electrode is of an annular configuration. The pole of the first electrode is also arranged within the annular pole of the second electrode. The configuration and relative arrangement of the two poles on the end face make it possible for locally clearly circumscribed regions of the tissue bearing thereagainst to be affected by a high frequency ac voltage, more specifically in a highly uniform manner over the entire electrode tip.

In accordance with a further preferred embodiment the first electrode is tubular at least in the region of the distal end of the shank, wherein a distal end of the tubular first electrode forms the pole in the end face. Alternatively the first electrode can assume the shape of a sleeve at least in the region of the distal end, wherein a distal end of the first electrode forms the end of the sleeve or the pole in the end face. The second electrode is preferably also tubular in the region of the distal end, wherein a distal end of the tubular second electrode forms the pole in the end face. Manufacture of the coagulation electrode can be simplified by the specified configurations for the electrodes so that manufacturing costs are reduced. In addition the configuration of the electrode tip imparts the stability necessary for handling. Finally, the variant set forth in the preceding paragraph, with an outer annular pole, can be particularly easily implemented with electrodes which are already tubular. The variant with a first electrode in sleeve form, in combination with the temperature control unit, is to be particularly implemented in terms of production engineering.

A further preferred configuration of the bipolar coagulation probe—which can also be embodied without the temperature control unit according to the invention—also has a distal end having an end face in which a pole of a first electrode and a pole of a second electrode are integrated. The bipolar coagulation probe is therefore suitable for surface coagulation. In addition the bipolar coagulation electrode includes at least one further electrode with a pole arranged at the periphery of the shank. A second pole on the periphery of the shank can be formed by the annular pole, which is prolonged in the proximal direction, in the end face of the coagulation probe, in other words, the coagulation probe shank which adjoins the end face has at least two poles. The coagulation probe thus has two electrodes which are suitable for interstitial coagulation. Preferably a pole arranged at the periphery of the electrode tip extends in an annular configuration around the shank as that permits spatially clearly defined treatment of the tissue. In accordance with a variant which is particularly simple to implement in terms of circuit engineering and which is suitable both for interstitial and also bipolar surface coagulation, one of the electrodes of the coagulation electrode forms both a pole in the end face and also a pole at the periphery of the electrode tip. That de facto affords a common pole having two pole surfaces so that a combined coagulation probe for bipolar surface coagulation and bipolar interstitial coagulation has overall three poles of which two non-adjacent poles can be electrically connected together. In this embodiment the coagulation probe preferably has only three electrodes. The above-mentioned particular embodiment of the bipolar coagulation electrode both for surface coagulation and also for interstitial coagulation can preferably include the above-described temperature control unit in all the variants thereof.

Figure 2:
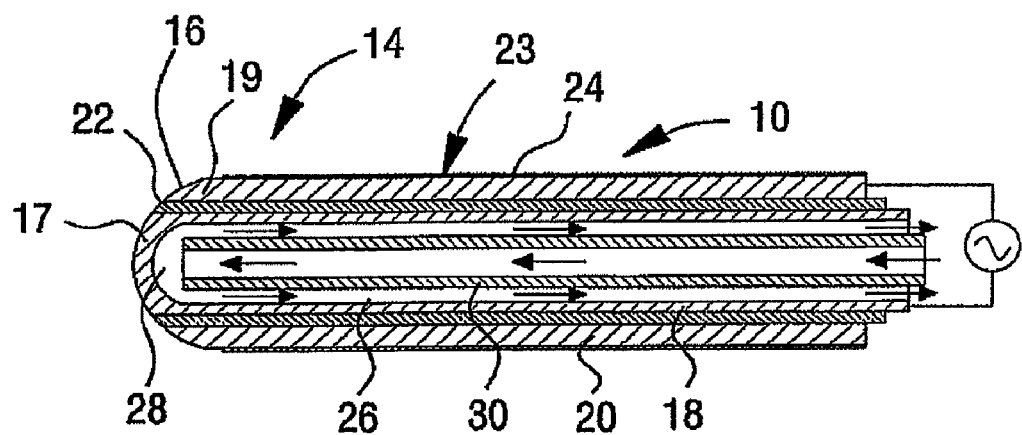
Figure 3:
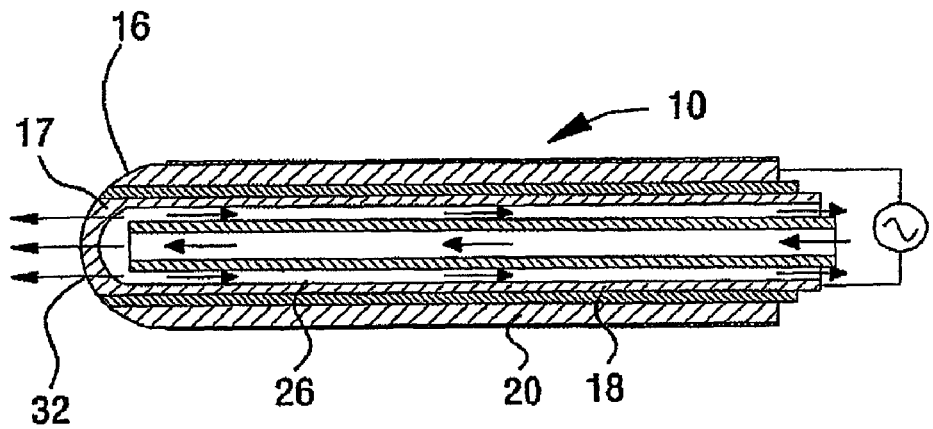
Figure 4:
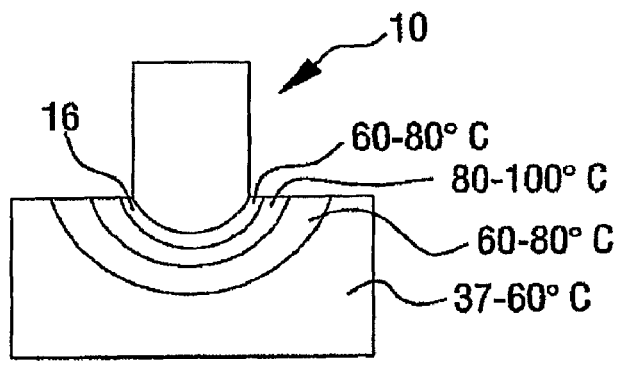
Figure 5:
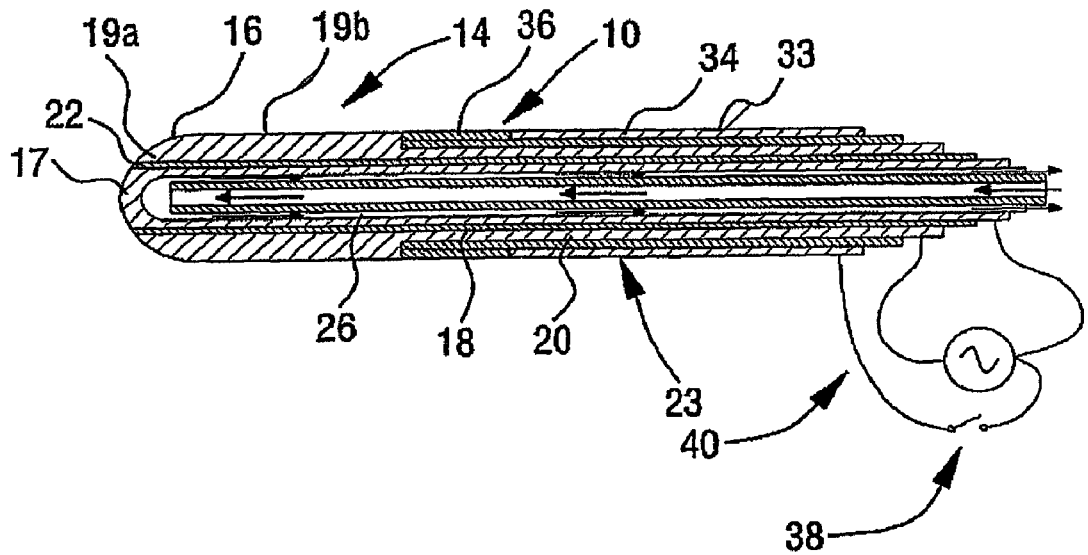

The invention is described in greater detail hereinafter by means of embodiments by way of example and with reference to the accompanying drawings in which:

FIG. 1 shows a plan view of a bipolar coagulation probe,

FIG. 2 shows a view in longitudinal section through a bipolar coagulation probe with a temperature control unit in accordance with a first variant, FIG. 3 shows a view in longitudinal section through a bipolar coagulation probe with a temperature control unit in accordance with a second variant with partial fluid discharge for preventing tissue from drying out, FIG. 4 shows a temperature profile during the coagulation with a temperature-controlled coagulation probe, and FIG. 5 shows a view in longitudinal section through a bipolar coagulation probe with a temperature control unit in accordance with a third variant for surface and interstitial coagulation.

FIG. 1 shows a bipolar coagulation probe 10 which fits in a guide shank of an endoscope 12 (not shown in greater detail here). The coagulation probe 10 has a shank 23 having a distal end 14 formed by a spherical end surface 16. Two electrically mutually insulated, electrical poles 17, 19 of a first and a second electrode 18, 20 are integrated in the spherical end face 16. The coagulation probe 10 can be used for surface coagulation.

FIG. 2 diagrammatically shows a view in longitudinal section illustrating the structure of the coagulation probe 10 of FIG. 1. As can be seen the end face 16 is of a spherical configuration and at its surface is divided into portions which are formed by the poles 17, 19 of the first and second electrodes 18, 20 and an insulator 22 separating the two electrodes 18, 19. In this embodiment the end face 16 is virtually in the form of a hemisphere forming a rounded-off transition to the shank 23.

The first electrode 18 is in the form of a metal sleeve which is closed at its distal end. The closed end of the metal sleeve is arranged centrally in the end face 16 of the electrode tip 14 and there forms the pole 17. The second electrode 20 is in the form of a metal tube which is covered by a thin insulator layer 24 in the region of the shank 23. A distal end of the second electrode 20 forms the pole 19. When an ac voltage is applied a current now flows in the region of the spherical end face 16 by way of the tissue bearing thereagainst, between the two poles 17, 19 of the electrodes 18, 20. As a consequence thereof the tissue is heated and coagulated. In a coagulation electrode which is not temperature controlled, the highest temperature prevails in the region of the tissue which bears against the poles 17, 19 of the electrodes 18, 20. The result of this can be that, as the tissue increasingly dries out, it progressively adheres to the poles 17, 19 of the electrodes 18, 20.

To avoid the above-mentioned effect, a temperature control unit 26 is integrated into the coagulation electrode 10. The temperature control unit 26 includes a guide structure 28 which is arranged at the rear side of the end face 16 and by way of which an afflux flow of temperature control medium is diverted and guided back again. A sterile, pyrogen-free physiological saline solution or deionised water is used as the temperature control medium. In the present case for implementing the guide structure 28 the temperature control unit 26 includes a tube 30 which is arranged approximately centrally in the shank 23 and in which the temperature control medium is conveyed to the rear side of the end face 16 by a peristaltic pump (not shown here), as well as a concave structure arranged at the rear side of the end face 16. The guide structure 28 guides the temperature control medium back past the tube 30 on the outside thereof. A direction of flow of the temperature control medium is indicated by the illustrated arrows. In the variant illustrated here of the temperature control unit 26 the pole 19 of the second electrode 20 is less effectively cooled in comparison with the pole 17 of the first electrode 18. In such a situation a desired reduction in the electrode surface temperature can be achieved by the electrical pole 19 of the second electrode 20 being of a correspondingly larger configuration in order to reduce the current density and thus the heating effect. The temperature control unit 26 also includes means (also not shown here) for temperature control of the temperature control medium. Those means can include for example a thermostat of usual design which is connected into the circuit of the temperature control medium.

FIG. 4 diagrammatically shows a temperature profile which is set in temperature control of the coagulation electrode 10. As will be seen, a temperature which is critical in terms of tissue adhesion is not achieved by virtue of the temperature control of the poles 17, 19 (not shown in detail here) at the spherical end faces 16. Rather, the zone of the critical temperature is displaced into deeper tissue layers. It is possible in that way to effectively prevent the tissue sticking.

FIG. 3 shows a further variant of the coagulation electrode 10. The structure of the coagulation electrode 10 substantially corresponds to the structure which has already been shown in FIG. 2 so that attention is directed thereto. The sole difference is that the region of the spherical end face 16 of the pole 17 of the first electrode 18 has small bores 32 through which the temperature control medium of the temperature control unit 26 can issue. In this case the temperature control medium is a sterile, pyrogen-free physiological saline solution. A part or also the entire amount of the temperature control medium which is pumped through the coagulation electrode 10 issues from the small bores 32 in the end face 16 and wets that electrode region with electrically conducting fluid. As a result, the tissue drying effect which occurs when the tissue is subjected to a strong heating action can be compensated and electrical energy input can be improved by virtue of maintaining the electrical conductivity of the tissue.

The coagulation electrode 10 in FIG. 5 combines the properties of a bipolar interstitial coagulator and a surface coagulator and in structure is based on the variant in FIG. 2. In this embodiment the pole 19 is prolonged in a proximal direction on the surface of the shank so that, besides the pole surface 19a in the end region of the probe, there is a further pole surface 19b at the periphery of the shank. The two poles 17, 19a, arranged at the end face 16, of the electrodes 18, 19 act as a surface coagulator while an ac voltage is applied to the two poles 19, 33 of the electrode 20, 34 for interstitial coagulation.

The second electrode 20 has a pole 19 with a pole surface 19a both in the region of the spherical end face 16 and also a pole surface 19b at the periphery of the electrode tip 14, that is to say on the shank 23. For interstitial coagulation both pole surfaces 19a and 19b co-operate as one pole 19. The second electrode 20 is separated from the third electrode 34 by an insulator 36. The temperature control unit 26 corresponds to the temperature control unit of FIG. 2 and is therefore not described in greater detail at this juncture.

The combined coagulation probe shown in FIG. 5 accordingly has a total of three electrodes 18, 20, 34 which form the poles 17, 19a, 19b and 33. By closing the switch 38 of the circuit 40 the coagulation electrode 10 can be switched over in function from a pure surface coagulator to an interstitial coagulator. The electrodes 18 and 34 are at the same potential so that coagulation is certain to be produced around the electrode tip 14. When selecting the pole sizes, consideration is to be given to the fact that the electrode 20 and in particular the electrode 34 are not directly temperature-controlled as they are not directly in contact with the circulating temperature control medium but are separated from the temperature control medium by a plurality of insulation layers 22, 36 as well as the metal tube of the electrode 18 or the metal tube of the electrode 20 respectively. With a desired reduction in the electrode surface temperature, the surface of the poles 19a, 19b, 33 of the electrodes 20, 34 is to be correspondingly enlarged in order to reduce the current density and thus the heating effect.

The invention claimed is:

1. A bipolar coagulation probe having a shank and a proximal end and a distal end and an end face at the distal end of the shank, in which a pole of a first electrode and a pole of a second electrode are integrated, characterized in that the coagulation probe includes a temperature control unit which is configured to temperature-control the coagulation probe in the region of its distal end by means of a temperature control medium; and further characterized in that the first electrode has the form of a metal sleeve with a spherical end surface at least at the distal end, the metal sleeve is arranged centrally at the distal end and forms the pole of said first electrode, and said pole of said first electrode is surrounded by the second electrode which is tubular at the distal end, whereby the metal sleeve forming the pole of the first electrode is surrounded by the second pole of the second electrode, wherein the temperature control unit includes a guide structure for the temperature control medium, with which the temperature control medium is guided to a rear side of the end face and from there at least partially deflected and guided back again; and wherein the guide structure includes a tube which is located substantially centrally within the shank and in which the temperature control medium is conveyed to the rear side of the end face and the guide structure guides the temperature control medium back past the tube on an outside of the tube.

2. A coagulation probe as set forth in claim 1 characterized in that the temperature control medium is a sterile, pyrogen-free physiological saline solution.

3. A coagulation probe as set forth in claim 1 characterized in that the temperature control medium is deionised water.

4. A coagulation probe as set forth in claim 1 characterized in that the temperature control unit is connected to a peristaltic pump.

5. A coagulation probe as set forth in one of claim 1 characterized in that the end face has bores through which the temperature control medium can issue.

6. A coagulation probe as set forth in claim 1 characterized in that the first electrode is tubular at least in the region of the electrode tip, wherein a distal end of the tubular first electrode forms the pole in the end face.

7. A bipolar coagulation probe having a proximal and a distal end and an end face at the distal end of a shank, in which a pole of a first electrode and a pole of a second electrode are integrated, wherein the coagulation probe includes a temperature control unit which is configured to temperature-control the coagulation probe in the region of its distal end by means of a temperature control medium, wherein:

said first electrode has a form of a sleeve with a spherical end surface at least in the region of the distal end of the shank, wherein a distal end of said first electrode forms a bottom of the sleeve and said pole of said first electrode in said end face; and said second electrode is tubular at least in the region of the distal end of said shank, wherein a distal end of said tubular second electrode forms said pole of said second electrode in said end face;

said pole of said second electrode has a surrounding configuration and said pole of said first electrode is arranged within said surrounding pole of said second electrode, wherein, the temperature control unit includes a guide structure for the temperature control medium, with which the temperature control medium is guided to a rear side of the end face and from there at least partially deflected and guided back again, and wherein the guide structure includes a tube which is located substantially centrally within the shank and in which the temperature control medium is conveyed to the rear side of the end face and the guide structure guides the temperature control medium back past the tube on an outside of the tube.

8. A coagulation probe as set forth in claim 7, wherein the temperature control medium is a sterile, pyrogen-free physiological saline solution.

9. A coagulation probe as set forth in claim 7, wherein the temperature control medium is deionised water.

10. A coagulation probe as set forth in claim 7 characterized in that the temperature control unit is connected to a peristaltic pump.

11. A coagulation probe as set forth in one of claim 7, wherein the end face has bores through which the temperature control medium can issue.

* * * * *